United States Patent [19]

Barry et al.

[11] Patent Number: 4,805,636

[45] Date of Patent: * Feb. 21, 1989

[54] SYSTEM FOR CONTROLLING MUSCLE RESPONSE

[75] Inventors: Daniel T. Barry, Ann Arbor, Mich.; Raphael A. Monsanto, Cranford, N.J.

[73] Assignee: The University of Michigan, Ann Arbor, Mich.

[*] Notice: The portion of the term of this patent subsequent to Feb. 25, 2003 has been disclaimed.

[21] Appl. No.: 124,348

[22] Filed: Nov. 20, 1987

Related U.S. Application Data

[63] Continuation of Ser. No. 832,830, Feb. 24, 1986, abandoned.

[51] Int. Cl.⁴ .......................... A61B 7/00; A61B 5/10; A61N 1/36; A61F 2/70
[52] U.S. Cl. ................................... 128/773; 128/774; 128/421; 128/905; 623/24
[58] Field of Search ................ 128/421–423, 128/733, 773, 774, 905; 623/24-25

[56] References Cited

U.S. PATENT DOCUMENTS

| 4,291,705 | 9/1981 | Severihehaus et al. | 128/733 |
| 4,569,352 | 2/1986 | Petrofsky | 128/423 W |
| 4,571,750 | 2/1986 | Barry | 128/774 X |
| 4,582,049 | 4/1986 | Ylvisaker | 128/423 W |
| 4,586,510 | 5/1986 | Glaser et al. | 128/423 W |

Primary Examiner—Kyle L. Howell
Assistant Examiner—John C. Hanley
Attorney, Agent, or Firm—Rohm & Monsanto

[57] ABSTRACT

A system for controlling muscular responses in living beings utilizes electrical stimulation of the muscle and acoustic monitoring of muscle performance. In one aspect, muscle functioning during a physical activity can be monitored acoustically, and the resulting signal compared against predetermined signal characteristics. Deviation of the muscle function from the desired characteristic can be corrected by applying a responsive electrical signal. Additionally, the response of a muscle to electrical stimulation can be monitored acoustically and an appropriate responsive correction to the electric signal, such as in its amplitude, frequency, spectral composition, duty cycle, can be made. In this manner, the invention permits control of muscle functions in dynamic and static states.

10 Claims, 2 Drawing Sheets

SYSTEM FOR CONTROLLING MUSCLE RESPONSE

This application is a continuation of application Ser. No. 832,830, filed Feb. 24, 1986, now abandoned.

BACKGROUND OF THE INVENTION

This invention relates generally to arrangements and methods for controlling muscle responses in living beings, and more particularly, to a system for controlling muscle response using electrical stimulation of the muscle and acoustic monitoring of a muscle response.

A large number of efforts are documented in the prior art for stimulating living beings electrically to achieve a desired response. In some known arrangements, electrical stimulation is applied to the nerves, illustratively during certain tumor removal operations, so that the resulting twitching or motion of the muscle at the nerve ending indicates communication between the tumor and the nerve. In such neurosurgical situations, the electrical stimulation is used as a form of continuity test which facilitates the surgery and reduces the risk of damage to the nerves. In addition to the foregoing, the prior art has provided a relatively large number of systems for electrically treating bodily tissues. More particularly, electrical stimulation apparatus has been used in therapy. Such therapy includes treatment of spinal curvature and the application of electrical stimulation to leg muscles in response to locomotion of the patient.

It is a problem with all known electrical stimulation arrangements and methods that information cannot easily be obtained with respect to the actual muscle response. Thus, for example, an electrically stimulated muscle will eventually tire or otherwise decouple from the stimulation and fail to respond. There is therefore a need for a system which permits monitoring of actual muscle functioning in response to the electrical stimulation.

Considerable effort has been expended in prior years toward the extraction and analysis of electrical signals generated within living boides. Of particular interest here are myoelectric signals which are understood to be representative of electrical excitation in skeletal muscles. It is now understood that myoelectric signals originate with the depolarization of the membranes of cells of individual muscle fibers during contraction. Such depolarization causes the generation of electrical potentials and currents which are detectable at remote locations, such as the surface of the skin. Thus, non-invasive techniques can be used to obtain the myoelectric signals, and therefore, such signals have been useful in controlling elementary prosthetic devices.

Ordinarily, myoelectric signals are obtained by placing an electrode, which may be made of a conductive, non-corrosive metal, such as silver or gold, on the surface of the skin of a living being. It is now well known that the placement of the electrode on the surface of the skin is a critical maneuver since precise placement of the electrode on the skin is required if a satisfactory signal detection is to be achieved. Generally, any slippage of the electrode from its initial location will degrade signal transmission.

In addition to the foregoing, myoelectric signal detection is adversely affected by variations in skin condition. For example, the impedance of the electrical communication between the electrode and the skin is altered substantially by the presence of perspiration. Thus, the electrical characteristics of the coupling to the skin of the electrode vary with skin condition. This is a substantial disadvantage of systems which rely upon myoelectric signals, in view of the very small amplitude of such signals.

In addition to requiring direct contact with the skin, myoelectric systems are subject to disruption by the presence of stray electrical fields. Accordingly, substantial electrical shielding is required, thereby increasing the cost and complexity of such systems.

It is a further problem with myoelectric signals that they do not contain within them complete information which characterizes muscular activity. In other words, the myoelectric signals are not representative of muscle activity, particularly after the onset of fatigue. During fatigue, excitation-contraction coupling is substantially reduced, and may in fact be near zero. Under such conditions, electrical activity of a muscle, as evidenced by the characteristics of a myoelectric signal, may appear to be normal, but little or no muscle contraction may be present. Thus, there is a need for a system which can assist in the determining of the onset of fatigue.

It has been known at least since the early nineteenth century that a rumbling-type of noise is produced when muscles are contracted. This noise-making capacity of skeletal muscles was publicized in the publication *Philosophical Transactions of the Royal Society*, pages 1-5 (1810). In this early lecture, Doctor William Hyde Wollaston describes a noise produced by contracting musculature having a frequency generally between 20 and 30 cycles per second, and amplitude which varies with the degree of force exerted by the muscle.

Much more recently, Doctors Oster and Jaffe reported in the *Biophysical Journal*, Vol. 30, April 1980, pp. 119-128, in a paper entitled "Low Frequency Sounds From Sustained Contraction of Human Skeletal Muscle," that the sound produced by a muscle grows louder with the increased loading. The sound is quite loud at the commencement of the loading, but rather quickly settles to a steady volume. Such a sound is further reported as arising in the muscles themselves, and is not of vascular origin.

The acoustic signals generated by muscles, in the form of a relatively low frequency rumbling noise, can be detected by a transducer, such as a microphone, which need not be placed in direct communication with the surface of the skin. In fact, the skin can be covered by a sock. Such a covering may be particularly useful in situations where skin conditions, such as those requiring dressing or ointment, render direct communication between the microphone transducer and the skin undesirable. However, the amplitude of the acoustic signal received by the transducer decreases substantially absent direct communication between the transducer and the skin, and of course, with distance from the skin.

It is, therefore, an object of this invention to provide a system for obtaining an indication of actual muscle performance in response to electrical stimulation thereof.

It is another object of this invention to provide a system wherein electrical stimulation of a living being is controlled in response to muscle performance.

It is a further object of this invention to provide a system wherein muscle performance is monitored and compared to a predetermined performance standard, and a corrective electrical stimulation is applied as required.

It is also an object of this invention to provide a system for correcting muscle performance.

It is yet another object of this invention to provide a system for monitoring muscle function in response to electrical stimulation wherein the muscle function monitoring is achieved without being affected by skin condition, or changes in skin condition over time, such as impedance changes which occur as a result of perspiration.

It is yet a further object of this invention to provide a system for controlling muscle function wherein muscle activity is monitored without requiring contact with the skin.

It is also another object of this invention to provide a system for correcting muscle-related postural problems.

It is still another object of this invention to provide a system for evaluating, diagnosing, and correcting dynamic muscular problems, such as those which result in improper gait.

It is still a further object of this invention to provide a system for controlling muscle responses to electrical stimulation, the system being generally unaffected by nearby electrical fields.

It is yet still another object of this invention to provide a system which detects muscle fatigue.

SUMMARY OF THE INVENTION

The foregoing and other objects are achieved by this invention which provides a system for producing a controlled muscle response. In accordance with the invention, an electrical signal is applied to stimulate a muscle of a living being. An acoustic signal generated within the muscle and responsive to the activity thereof is monitored.

In accordance with a further aspect of the invention, muscle activity is controlled by monitoring an acoustic signal from a muscle, responsive to the activity thereof, and applying an electrical signal to stimulate the muscle in response to the acoustic signal. In an illustrative embodiment of this invention, the acoustic signal is analyzed to obtain a value of a selected parameter thereof, illustratively amplitude, frequency, spectral composition, or any other selected parameter or combinations of parameters. The value of such a parameter, or parameters, can be compared to selected predetermined values which may be stored in a memory or generated by an algorithm. The result of the comparison between the monitored and stored parameter values may be applied, in certain embodiments of the invention, to control the electrical signal applied to the muscle of the living being.

In certain applications of the inventive system, it is desirable to monitor changes in the parameter values of the acoustic signal over time. Thus, the electrical stimulation of the muscle can be adjusted, or even discontinued, in response to predetermined muscle states, such as the onset of fatigue. Continued stimulation of a muscle in extreme fatigue is characterized by excitation-response decoupling. It is known that permitting a muscle to assume this decoupling state will probably result in partial destruction of the muscle tissue and a net deleterious effect.

In the practice of the invention, an acoustic sensor is used to provide a sensor electric signal responsive to the activity of the muscle of the living being. Additionally, an electric signal generator is used to produce the stimulating electric signal which is applied to the muscle. Electrical communication between the electric signal generator and the muscle of the living being is achieved by an electrode which, in certain embodiments, conducts the stimulating electric signal from an output of the electric signal generator to the skin of the living being.

Control of the overall muscle response is achieved by a feedback arrangement which modifies one or more parameters of the electric signal in response to the sensor electric signal. Thus, in a specific illustrative embodiment of the invention, a loop is formed wherein muscle activity is monitored by the acoustic sensor and the resulting sensor electric signal is applied to control the electric signal generator which produces a stimulating electric signal which is applied to the living being by an electrode.

BRIEF DESCRIPTION OF THE DRAWING

Comprehension of the invention is facilitated by reading the following detailed description in conjunction with the annexed drawing, in which.

DETAILED DESCRIPTION

The description herein incorporates by reference the disclosure of copending patent application Ser. No. 581,949, assigned to the same assignee as herein.

Figure 1:
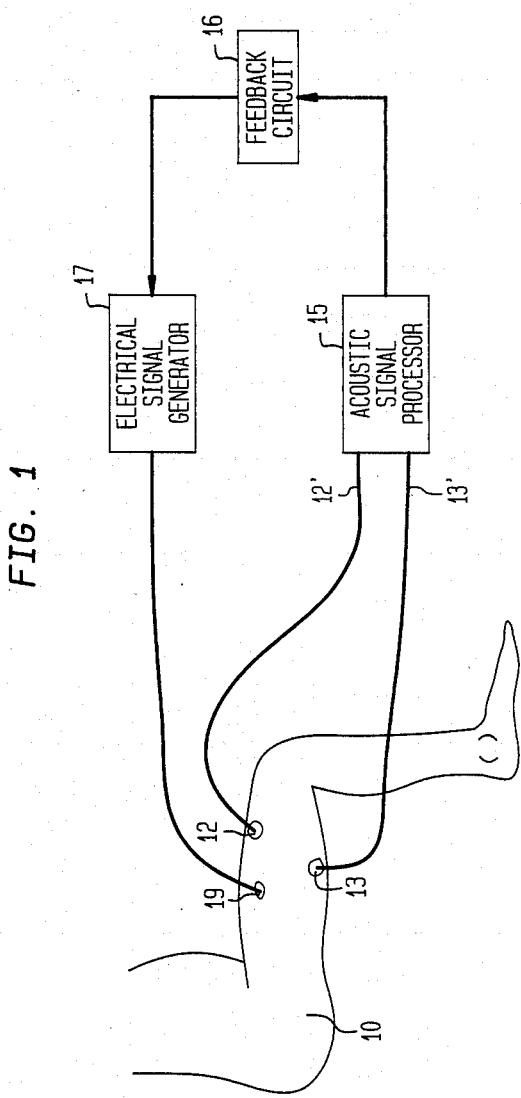
FIG. 1 is a function block diagram of a system for controlling muscle response.

FIG. 1 is a function block diagram of a circuit system for controlling a muscle response of a living being. As shown in this figure, human being 10 has coupled thereto a transducer 12, which may be a microphone, connected to an acoustic signal processor 15. Transducer 12 is arranged in the vicinity of the leg extensor muscles of the human being. A further transducer 13 is arranged in the vicinity of the leg flexor muscles. Transducer 13 is similarly connected to acoustic signal processor 15.

Figure 2:
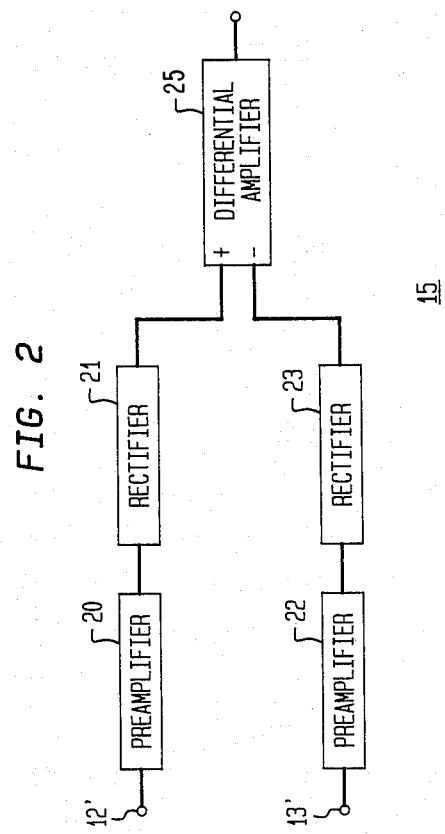
FIG. 2 is a function block diagram which illustrates a specific embodiment of the acoustic signal processing function block of FIG. 1.

FIG. 2 is a function block diagram of a specific illustrative embodiment of the circuitry of acoustic signal processor 15 of FIG. 1. Circuitry 15 of FIG. 2 includes a preamplifier 20 which receives at an input 12' thereof a signal from transducer 12. Preamplifier 20 is connected at its output to rectifier 21 which is subsequently coupled to a differential amplifier 25. A further preamplifier 22 receives at an input 13' thereof, a signal from transducer 13. Each of transducers 12 and 13, which may be microphones, produce at their output, and thereby deliver to respective preamplifier inputs 12' and 13', electrical signals which are responsive to the sounds of the muscles in the leg of human being 10. The electrical signal delivered at input 13' of preamplifier 22 is conducted through a rectifier 23 to a further input of differential amplifier 25.

Rectifiers 21 and 23 are coupled to noninverting and inverting inputs, respectively, of differential amplifier 25. The differential amplifier therefore produces at its output a signal which corresponds to the differences between outputs of the rectifiers. This signal is conducted to a feedback circuit 16, as shown in FIG. 1.

Feedback circuit 16 may incorporate therein a variety of known circuit elements. For example, the feedback circuitry may include a bandpass filter (not shown) which, in one embodiment, may be tuned in the vicinity of 20 Hz to 30 Hz. Additionally, the feedback circuit may contain an integrating circuit (not shown) which has a relatively long RC time constant, illustratively on the order of 0.2 to 1 second. The acoustic signals produced in the leg muscles of human being 10 have sufficient amplitude to permit transducers 12 and 13, in a practical embodiment of the invention, to produce output signals of 50 mV.

In addition to the foregoing, feedback circuit 16 may contain therein, in a specific illustrative embodiment, a comparator arrangement whereby values of selected parameters of the acoustic signal, illustratively amplitude, frequency, or spectral data, are compared against predetermined or stored parameter values. In such an embodiment, the signal which is produced at the output of feedback circuit 16 and conducted to electric signal generator 17 may be responsive to such filtering, integration, or comparisons.

The output signal of feedback circuit 16 drives electric signal generator 17. More particularly, the electric signal at the output of the electric signal generator is varied in certain respects in response to the signal received from the feedback circuit. In a simple case, for example, if acoustic energy at transducers 12 and 13 is insufficient, after being compared to a predetermined amplitude parameter value, the output signal of feedback circuit 16 is such that the amplitude of the electrical stimulation provided by electric signal generator 17 is increased. However, electric signal generator 17 may be provided with internal limiting circuitry which prevents the application of dangerously high electric signals to the living being. Thus, if it is determined that the amplitude of the electric stimulating signal from the electric signal generator has a maximum safe amplitude, and the acoustic energy produced at the transducers is too low, then, absent a circuit malfunction, it can be determined that muscle fatigue has set in.

It is to be noted that the response of the electric signal at the output of the electric signal generator to the signal produced by the feedback circuit need not be limited to variations in amplitude. Such responsive variations may include changes in frequency, spectral composition, waveform variations, and/or duty cycle changes. Persons skilled in the art can predetermine the electric signal parameters desired to be changed, for their particular applications.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A method of controlling muscle activity, the method comprising the steps of:

obtaining an acoustic signal from a muscle responsive to activity of said muscle; and
   applying an electric signal to said muscle responsive to said acoustic signal.

2. The method of claim 1 wherein prior to performing said step of applying there is provided the further step of comparing a selected characteristic parameter of said acoustic signal against predetermined values of said selected characteristic parameter.

3. The method of claim 2 wherein said step of applying is further responsive to said step of comparing.

4. The method of claim 2 wherein there is provided the further step of controlling said electric signal in response to said step of comparing.

5. A method of producing a controlled muscle response, the method comprising the steps of:

applying an electric signal from a signal generator to a muscle of a living being for producing a responsive contraction in said muscle;
   monitoring an acoustic signal generated by said muscle in response to said electric signal;
   producing a monitor signal responsive to said step of monitoring; and
   controlling said signal generator in response to said monitor signal, whereby said responsive contraction in said muscle is controlled.

6. The method of claim 5 wherein said step of producing a monitor signal comprises the further step of selecting a predetermined characteristic parameter of said acoustic signal, whereby said monitor signal is responsive to said selected predetermined characteristic acoustic signal parameter.

7. The method of claim 6 wherein there is provided the further step of comparing a value of said selected predetermined characteristic acoustic signal parameter to a predetermined value.

8. The method of claim 7 wherein there is provided the further step of monitoring variations in said value of said selected predetermined characteristic acoustic signal parameter over a predetermined period of time.

9. The method of claim 7 wherein there is provided the further step of monitoring variations in said value of said selected predetermined characteristic acoustic signal parameter in response to said electric signal.

10. A system for producing a controlled muscle response, the system comprising:

acoustic sensor means for producing a sensor electric signal responsive to a muscle of a living being;
    electric signal generator means having an output for producing a stimulating electric signal;
    electrode means for coupling said stimulating electric signal to said living being; and
    feedback means coupled to said acoustic sensor means for receiving at least a portion of said sensor electric signal, and to said electric signal generator means for controlling said stimulating electric signal in response to said sensor electric signal.

* * * * *